United States Patent [19]

Sikorski et al.

[11] Patent Number: 5,522,861
[45] Date of Patent: Jun. 4, 1996

[54] ACCESS GROMMET ASSEMBLY AND DEVICES USING THE ASSEMBLY

[75] Inventors: James M. Sikorski, Mounds View; Bruce W. Allen, Apple Valley; Jack A. Ronning, Mound, all of Minn.

[73] Assignee: Medtronic, Inc., Minneapolis, Minn.

[21] Appl. No.: 158,065

[22] Filed: Nov. 23, 1993

[51] Int. Cl.$^6$ ............................................ A61N 1/02
[52] U.S. Cl. ..................... 607/36; 174/65 R; 277/235 R
[58] Field of Search ........................ 607/1, 2, 36–38, 607/90; 16/2; 114/114; 292/314, 307 R; 227/55; 29/854–864, 874, 882, 883; 439/86, 91, 162–165, 207–211, 246–248, 252, 271–272, 278, 283, 927; 174/153 G; 248/56; 124/65 R; 277/135, 138, 175, 180, 235 R; 49/480.1, 483.1, 498.1, 499.1; 70/423

[56] References Cited

U.S. PATENT DOCUMENTS

| | | | |
|---|---|---|---|
| 96,654 | 11/1869 | Andrews | 277/235 R |
| 3,057,356 | 10/1962 | Greatbatch | 128/422 |
| 3,278,883 | 10/1966 | Lipsey | 439/927 |
| 3,396,979 | 8/1968 | Balkin et al. | 277/235 R |
| 3,845,961 | 11/1974 | Byrd, III | 248/56 |
| 4,314,562 | 2/1982 | Ware | 128/419 P |
| 4,400,920 | 8/1983 | Logsdon | 248/56 |
| 4,401,120 | 8/1983 | Hartlaub | 128/419 PT |
| 4,775,325 | 10/1988 | Wilson | 439/278 |
| 4,943,247 | 7/1990 | Wise | 439/927 |
| 4,958,632 | 9/1990 | Duggan | 128/419 |
| 5,052,388 | 10/1991 | Sivula | 128/419 PG |
| 5,080,096 | 1/1992 | Hooper | 128/419 R |
| 5,088,488 | 2/1992 | Markowitz | 128/419 PG |
| 5,127,404 | 7/1992 | Wyborny | 128/419 P |
| 5,154,170 | 10/1992 | Bennett | 128/419 PG |
| 5,303,937 | 4/1994 | Huss et al. | 277/235 R |
| 5,403,976 | 4/1995 | Maurice | 248/56 |

FOREIGN PATENT DOCUMENTS

| | | | |
|---|---|---|---|
| 0052879 | 6/1982 | European Pat. Off. | 607/37 |
| 0534782 | 3/1993 | European Pat. Off. | |
| 3522811 | 1/1987 | Germany | 49/483.1 |

Primary Examiner—William E. Kamm
Attorney, Agent, or Firm—Reed A. Duthler; Harold R. Patton

[57] ABSTRACT

An implantable medical device including a hermetic housing containing an electronic circuit, such as a cardiac pacemaker. The electronic circuit may be coupled to a medical lead by means of a connector module which is formed as part of a molded, resilient shroud, extending around the circumference of the hermetic container.

7 Claims, 8 Drawing Sheets

ACCESS GROMMET ASSEMBLY AND DEVICES USING THE ASSEMBLY

BACKGROUND OF THE INVENTION

The present invention relates to implantable medical devices and more particularly to methods of their manufacture.

The earliest pacemakers, for example as disclosed in U.S. Pat. No. 3,053,356 to Greatbatch, were manufactured of discrete electronic components which were potted in an epoxy resin material and then coated with silicone rubber. Continued progress in the development of heart pacemakers resulted in packaging concepts in which the electronic circuitry portion of the pacemaker was enclosed in a sealed metal container which was coupled to batteries outside the container. The batteries and sealed container were potted in epoxy to form the pacemaker.

Development of the solid state lithium iodide battery permitted the inclusion of the electrochemical cell within a hermetic metal housing. Such a pacemaker is disclosed in U.S. Pat. 4,314,562. In most such pacemakers, the pacemaker housing is formed from two metal halves, which form a "clam shell" assembly. The housing halves are typically butt welded together along their edges. Electrical communication to pacing and sensing electrodes in such pacemakers is accomplished using a rigid plastic connector module fixed to the outer surface of the housing and one or more feedthroughs which permit electrical communication to and from circuitry within the housing while retaining hermeticity of the pacer. This pacemaker architecture has become conventional, and has resulted in reliable long lived pacemakers. This basic architecture has also been employed to produce other types of implantable devices such as implantable defibrillators, nerve stimulators, drug pumps and physiologic monitors.

Construction of pacemakers or other implantable medical devices using the basic architecture described above has required solution of a variety of problems, the solutions to which in turn often require complex manufacturing operations which increase costs, lower yields and limit design freedom. Such manufacturing operations may include: the use of weld rings to protect internal components during butt welding operations to join the housing halves; welding interconnections between the battery, circuitry and feedthroughs; location of feedthroughs in areas adjacent to or on the seam joining the housing halves; fabrication of cups or spacers to locate the battery and circuitry within the housing; molding of plastic connector modules around electrical connector blocks and cosmetic buffing operations to improve the appearance and biocompatibility of the enclosure.

SUMMARY OF THE INVENTION

The present invention is directed to providing a pacemaker or other implantable medical device which can be produced more simply and inexpensively, while retaining the desirable durability and reliability of devices produced using the conventional architecture discussed above. The new device architecture provided by the present invention may be produced using fewer components and fewer manufacturing steps, and eliminates altogether many of the production operations described above.

In contrast to prior art structures, the present invention employs a device housing formed from a substantially planar lid which is welded to a circumferential flange formed on a deep drawn shield. The shield and lid form a device housing which is encased in a compliant shroud of an elastomer such as silicone rubber, which surrounds the edge of the housing, isolates the welded flange from direct body contact and provides a smooth, rounded contour along the edge of the device which enhances biocompatibility.

Within the context of this basic new device architecture, a number of specific improvements have been made according to the present invention. Rather than employing a plastic cup or insulator to locate the hybrid circuit and battery within the device housing, the hybrid circuit and battery are adhesively mounted directly to the shield. The adhesive serves to mechanically mount the components and may in some embodiments also serve to electrically insulate them from the shield. Because the adhesive firmly attaches the hybrid and battery to the shield, the assembly produced thereby is rigid, which in turn facilitates the use of wire bonding techniques to couple the battery to the circuitry and couple the circuitry to the feedthrough or feedthroughs. Each feedthrough to the exterior of the device is provided with a wire bonding pad, located parallel to wire bonding pads on the hybrid circuit, to further facilitate wire bonding operations. The resultant pacemaker assembly is sturdy, reliable and substantially less expensive to produce than a device employing butt-welded housing halves, an internal plastic cup and welded interconnections as are typically employed.

In a further aspect of the present invention, the connector module is formed as an integral part of the compliant shroud, rather than being formed as a separate, molded rigid plastic part as is presently conventional. The shroud is molded with a longitudinal connector bore, corresponding in general configuration to connector bores employed in previous connector modules. Because the connector block is located within a compliant, flexible structure, it is provided with a stabilizer bar, extending longitudinally from the connector housing, parallel to the connector bore, to prevent twisting of the connector block, relative to the shroud. Additionally, the wire connecting the connector block to its corresponding feedthrough is formed in an S-shaped configuration, providing strain relief to prevent fractures due to flexing of the wire within the compliant connector module.

In another aspect of the present invention, an enhanced mechanism for assuring sealing of the puncturable grommet associated with the connector block is provided. Like conventional connector housings, a pierceable grommet is provided to allow access to a set screw in the connector block. Rather than molding a separate grommet, the shroud itself is molded to provide a pierceable grommet, defining an access path aligned with the set screw in the connector block. In addition, adjacent the pierceable grommet, a shim is inserted, in a slot cut into the shroud, after molding. The shim compresses the material of the shroud on either side of the shim, including the material along the access path through the pierceable grommet. After tightening the set screw in the connector block, the set screw wrench is removed, and the compressive force provided by the shim assists in sealing the pierceable grommet along the access path to provide a water tight, high impedance seal.

DETAILED DESCRIPTION OF THE PREFERRED EMBODIMENT

Figure 1:
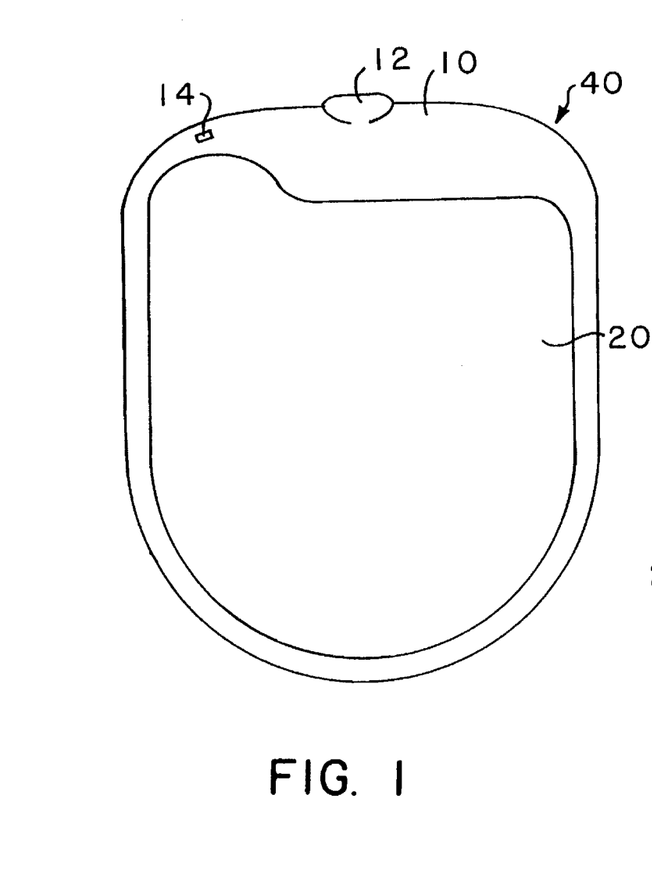
FIG. 1 is a plan view of the upper surface of an assembled pacemaker according to the present invention.

FIG. 1 is a plan view of the upper surface of a pacemaker according to the present invention. In this view, the lid 20 of the device housing is visible, surrounded by the shroud 10. Molded into shroud 10 is a pierceable grommet 12, a suture bore 14 for suturing the pacemaker to underlying tissue, and a connector bore having an entrance at 40, not visible in side view.

Figure 2:
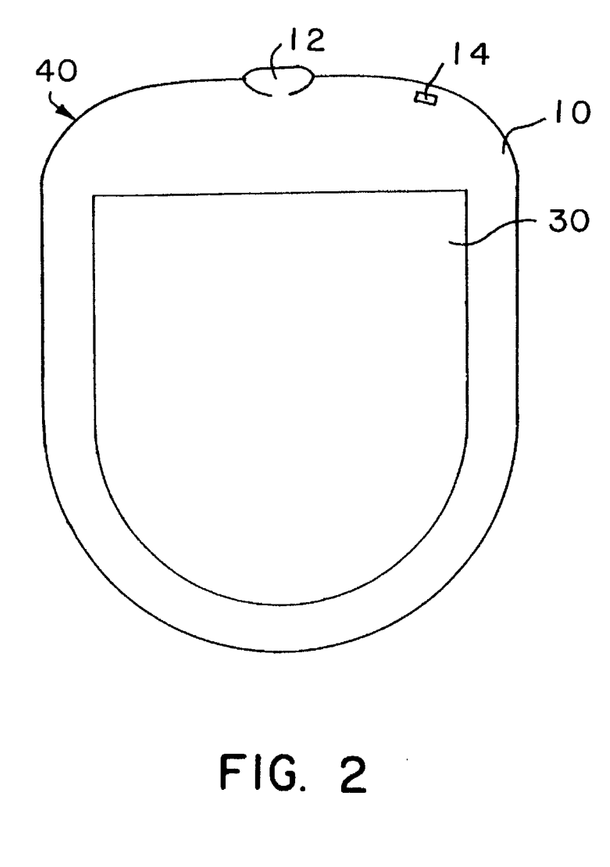
FIG. 2 is a plan view of the lower surface of the pacemaker illustrated in FIG. 1.

FIG. 2 is a plan view of the lower surface of the pacemaker illustrated in FIGS. 1 and 2. In this view, the generally planar lower surface of shield 30 is visible, surrounded by shroud 10. Grommet 12 and suture bore 14 are also visible, with the entrance 40 of the connector bore indicated as well.

Figure 3:
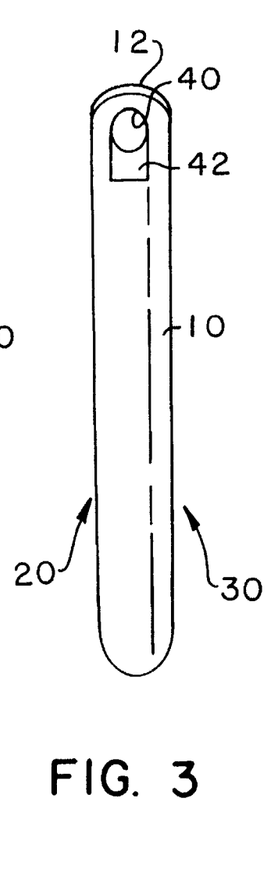
FIG. 3 is a plan view of an edge of the pacemaker illustrated in FIG. 1.

FIG. 3 is a plan view of the edge of the pacemaker illustrated in FIG. 1. In this view, the connector bore entrance 40 is visible, along with a radiused exit surface 42, to facilitate lead wrapping. The shroud 10 extends from the upper surface of the lid 20 to the lower surface of the shield 30, and provides a generally rounded contour extending between these two surfaces, around the circumference of the pacemaker.

Figure 4:
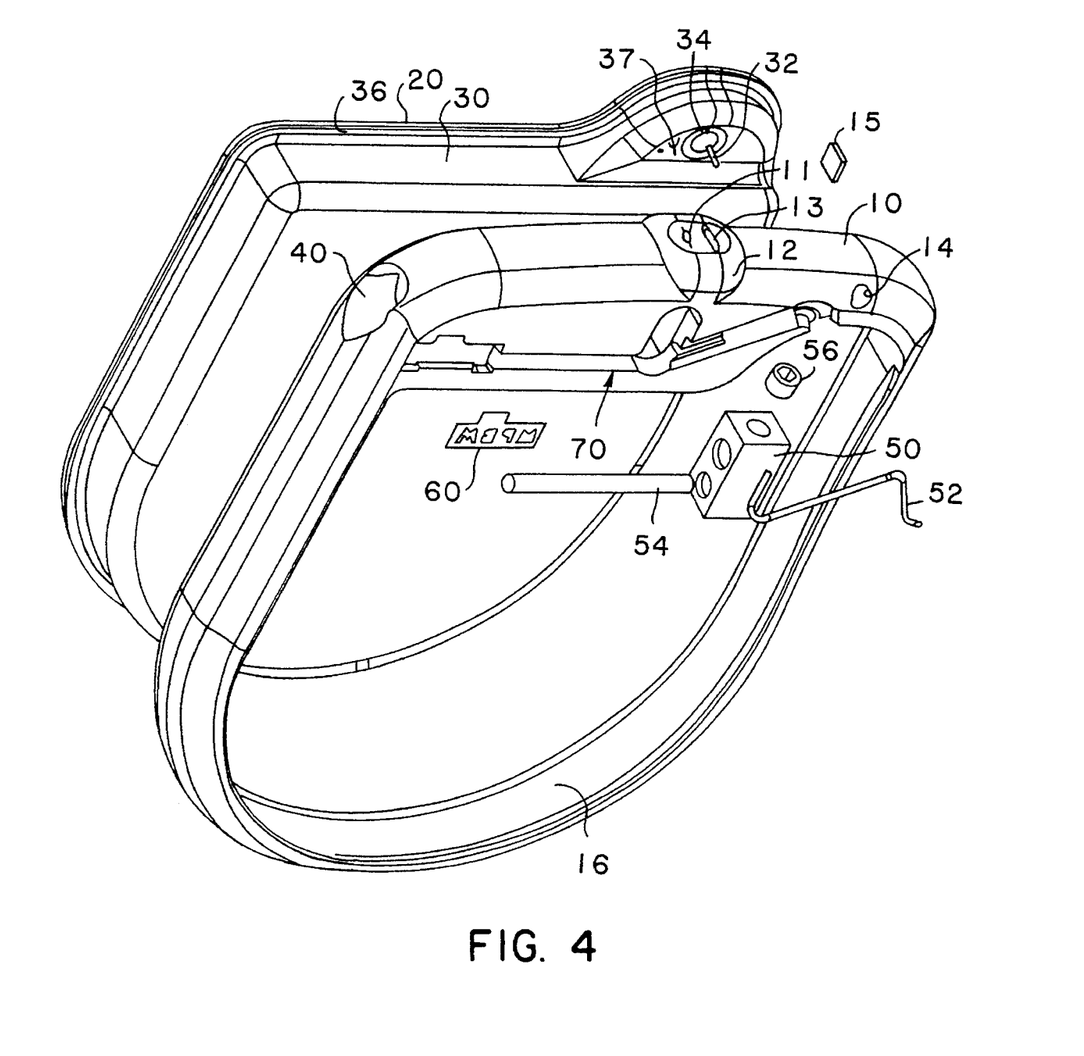
FIG. 4 is an exploded view of the major components of the pacemaker illustrated in FIGS. 1–3, particularly illustrating the components of the shroud, including the connector block, stabilizer bar and grommet shim.

FIG. 4 shows an exploded view of the shroud 10 and its associated components, in conjunction with the device housing as assembled. The device housing includes the lid 20 and the shield 30, which may be fabricated of titanium or other biocompatible metal, and have been welded together around their circumference along the flange 36, surrounding the edge of the shield 30. The housing provides a hermetically sealed enclosure which prevents fluid access to the battery and circuitry inside. Feedthrough 34 is shown mounted to shield 30, and having a feedthrough wire extending perpendicular to the lower surface of shield 30. Feedthrough 34 is laser welded around its circumference to shield 30. Shield 30 is drawn so that it displays a stepped configuration to define a planar surface 37, in which feedthrough 34 is mounted. Surface 37 is generally parallel to and above the generally planar lower surface of shield 30, with feedthrough wire 32 oriented perpendicular to the lower surface of shield 30.

In this view, the over all configuration of shroud 10 is more clearly visible. Shroud 10 is provided with a large central opening 16 which corresponds in configuration to the external periphery of the device housing. The integrated sealing grommet 12 is provided with a depression 11, indicating the appropriate place for insertion of a set screw wrench, defining the entry point of the access path to the set screw 56 in the connector block 50, when assembled. A second depression 13, indicates the area of insertion of shim 15, which serves to compress the shroud material in the vicinity of depression 11, assuring the ability of the grommet to reseal itself electrically along the access path, after removal of the set screw wrench.

Shroud 10 is also provided with an elongated recess 70 of complex configuration. Recess 70 serves to locate the radio opaque marker 60, connector 50, connector block wire 52 and stabilizer bar 54. Set screw 56 is shown removed from connector block 50. The elongated recess 70 is described in more detail in conjunction with FIG. 5, below.

Figure 5:
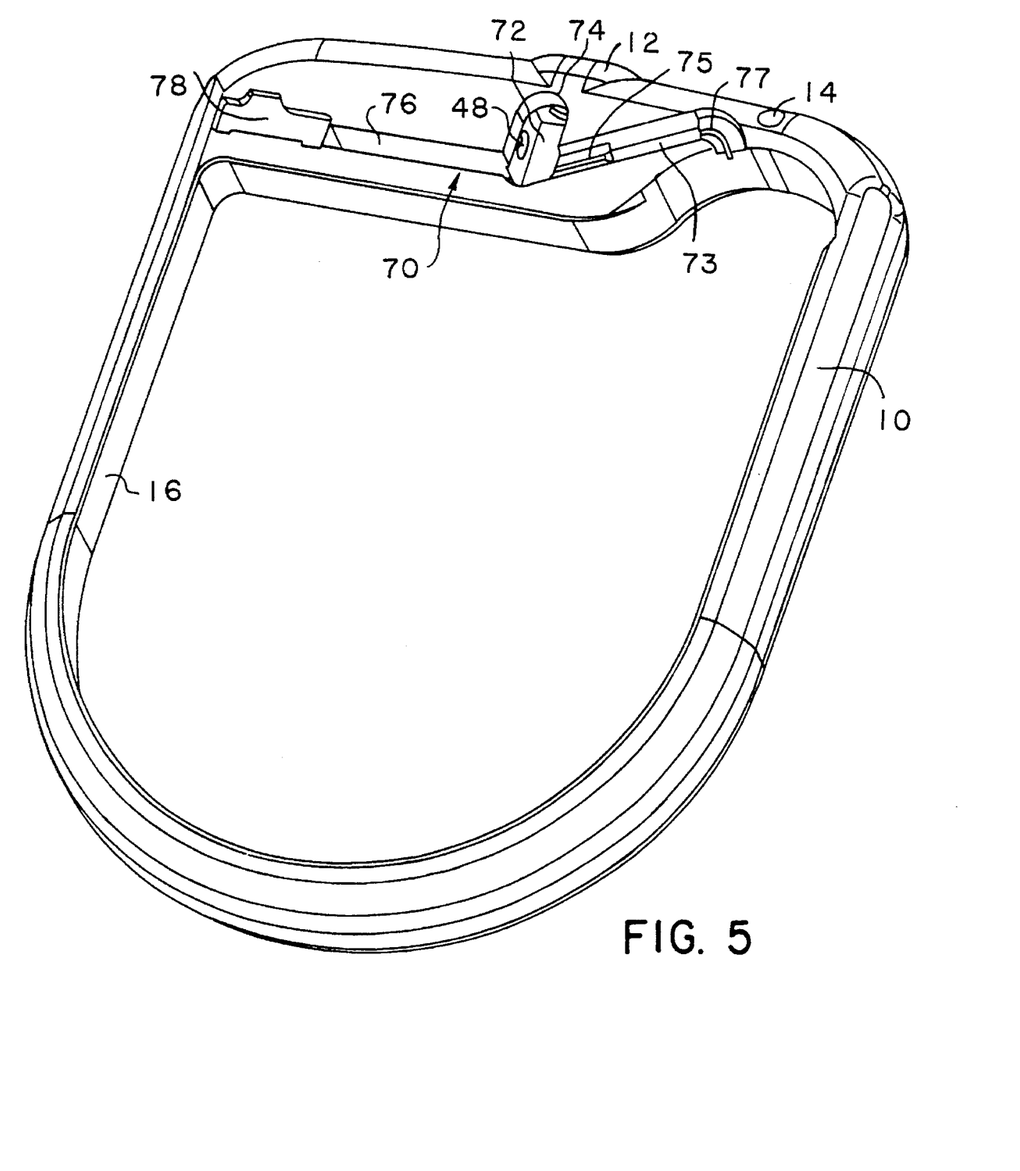
FIG. 5 is a perspective view of the shroud illustrated in FIG. 4, looking generally toward the lower surface of the shroud.

FIG. 5 shows shroud 10 in perspective view, looking at shroud 10 generally from its lower surface. In this view, the details of the elongated recess 70 are more clear. Located centrally within recess 70 is a chamber 72 for locating connector block 50 (FIG. 4). Chamber 72 is sized and shaped to correspond to the outer dimensions of connector block 50, and generally takes the form of a rectangular prism. Surrounding chamber 72 is a molded lip 74, which extends inward from the periphery of chamber 72, and serves to retain connector block 50, after insertion into chamber 72. Because shroud 10 is fabricated of a resilient, elastomeric material, such as silicone rubber, it is possible to deform the lip 74 in order to allow connector block 50 to be snapped into chamber 72. Chamber 72 is in communication with the proximal end 48 of the connector bore, so that a connector assembly of a pacing lead may be inserted into connector block 50 via the connector bore. Extending from chamber 72 is an elongated slot 76, which serves to receive the stabilizer bar 54, as illustrated in FIG. 4. Located at the end of elongated slot 76 is a recess 78, which receives the radio opaque indicator marker 60 (FIG. 4). Extending from chamber 72 opposite elongated slot 76 is a curved slot 73, which serves to receive connector block wire 52 (FIG. 4). Curved slot 73 is provided with two sections 75 and 77 which include narrower slots sized to frictionally engage the connector block wire 52, holding it in place during welding and backfilling operations. Grommet 12, suture bore 14 and central opening 16 are also indicated.

Figure 6:
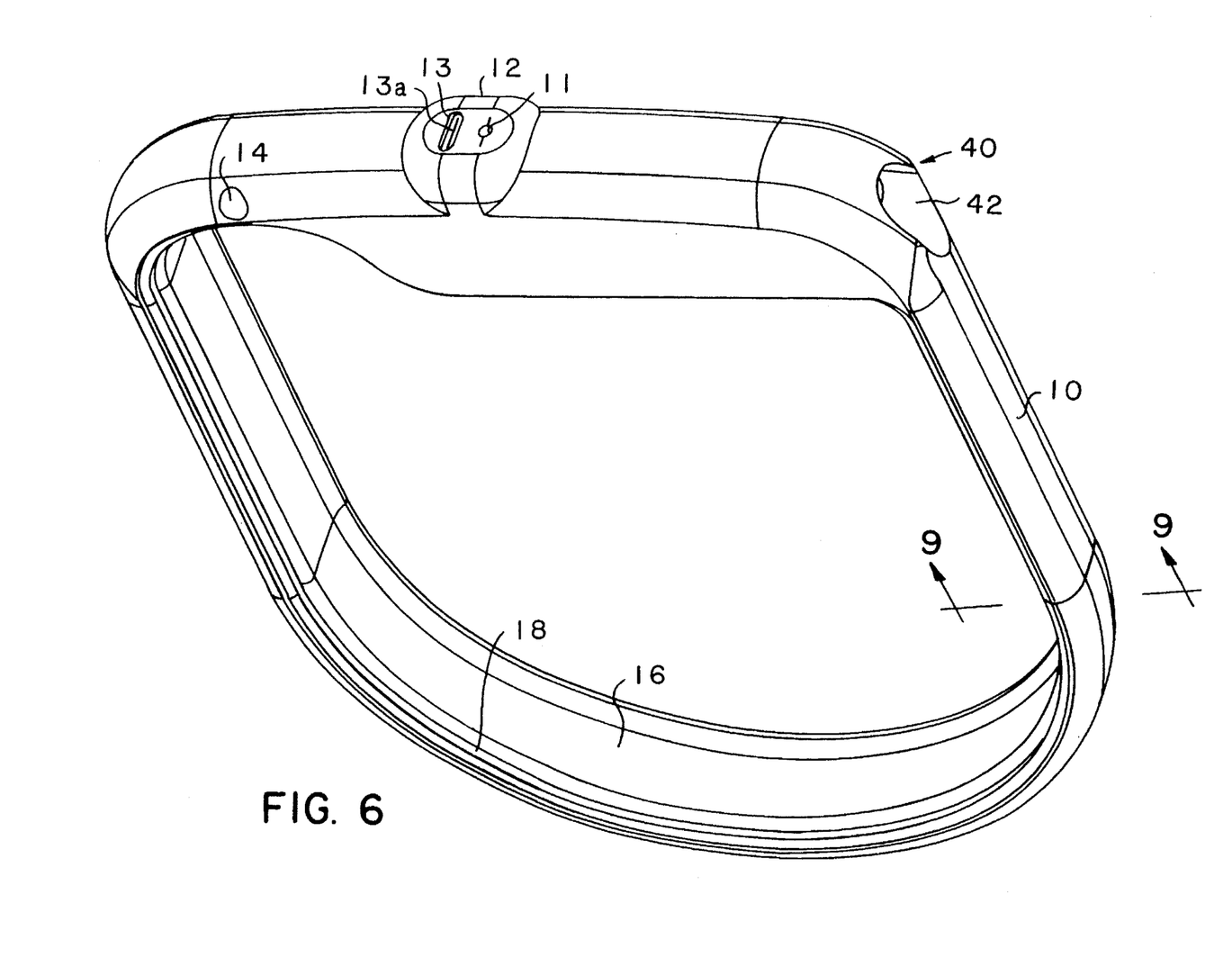
FIG. 6 is a perspective view of the shroud illustrated in FIG. 4, looking generally toward the upper surface of the shroud.

FIG. 6 is a perspective view of shroud 10, looking at the upper surface of the shroud. In this view, the depression 11, defining the point at which the set screw wrench is inserted into the grommet 12, as well as recess 13 are both visible. A slot 13a is cut into recess 13, to receive grommet shim 15. Also visible is the entrance into connector bore 40. In this view it can also be seen that the shroud 10 is provided with a circumferential internal groove 18, extending around the central opening 16 of the shroud, adjacent the upper surface of the shroud. This groove receives the outer edge of the lid 20 and the flange 36 of shield 30. Because the welded edges of the lid and shield are enclosed by the shroud, there is no requirement to buff or finish the welded area to improve the appearance of the device or enhance its biocompatibility. Entry 40 of the connector bore and associated radiused surface 42 are also illustrated.

Figure 7:
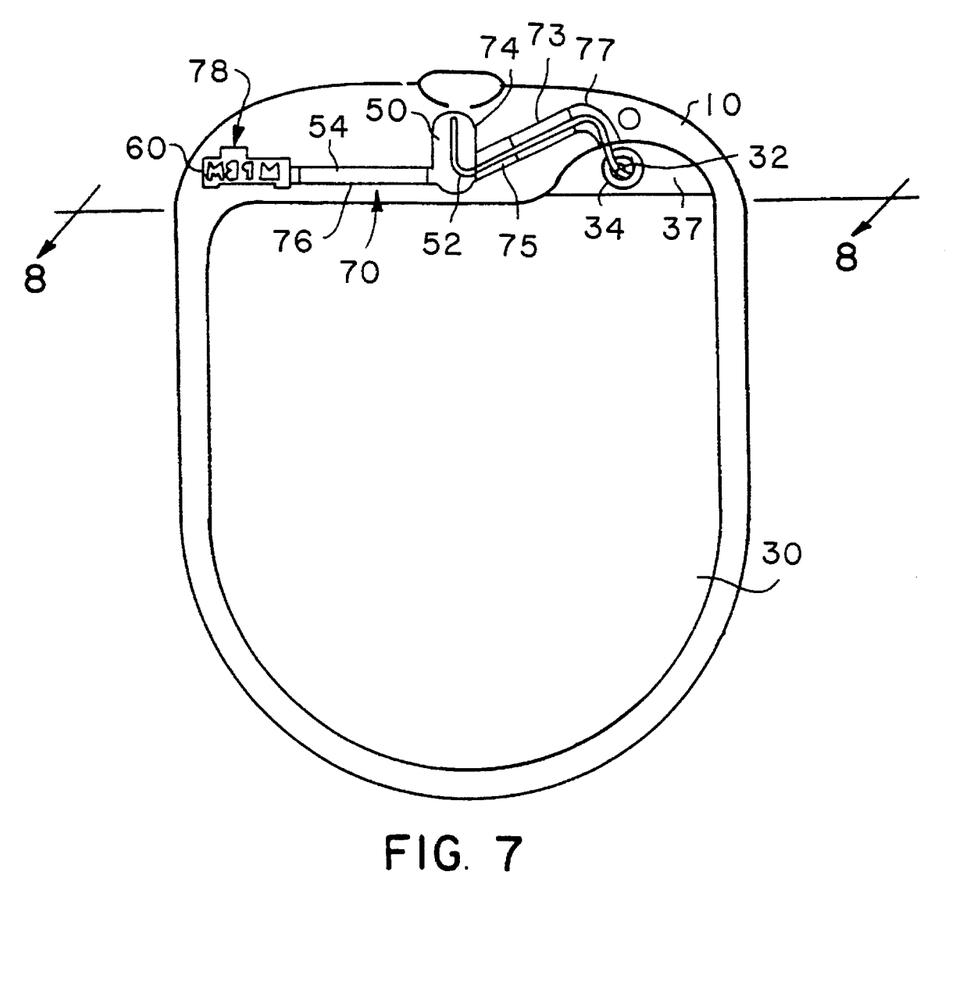
FIG. 7 is a plan view of the shroud, connector block, stabilizer pin, device housing and associated components as assembled, prior to backfilling.

FIG. 7 is a plan view of the lower surface of the pacemaker, showing the components illustrated in FIGS. 4, 5 and 6 as assembled. Shroud 10 has been attached to shield 30 and lid 20. The assembled housing is first snapped into the shield so that the welded edges of the lid 20 and shield 30 located in slot 18 (FIG. 6). Silicone rubber is then injected between the shroud 10 and the housing, around its periphery, using an automated adhesive dispenser. The mechanical interconnection of the shroud and the housing provided by the slot 18 allows for automation of this assembly step. Connector block 50 is snapped into recess 72 (FIG. 5) of shroud 10, and is held in place by lip 74. Connector block wire 52 is welded to the surface of connector block 50 and extends through curved slot 73, being frictionally retained within slot 73 by the grooves in areas 77 and 75. The end of connector block wire 52 is welded to feedthrough wire 32. Stabilizer bar 54 has been inserted into connector block 50, and is located within slot 76. Radio-opaque marker 60 has been located in area 78, as illustrated in FIG. 5. After all of the components illustrated have been assembled, the entire elongated recess 70 the area of surface 37 is backfilled with silicone rubber adhesive, to cover indicator 60, connector block 50, connector block wire 52 and feedthrough 34. The backfill completes the structure of the shroud, sealing the connector block and associated components within the shroud 10 and providing a smooth outer surface, providing a final configuration as illustrated in FIG. 2.

Figure 8:
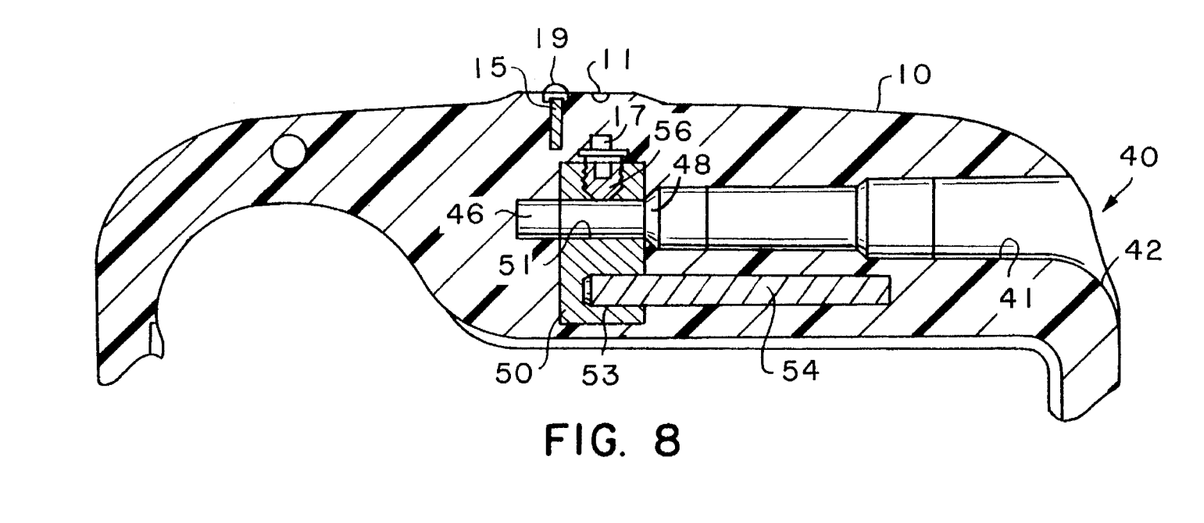
FIG. 8 is a sectional view through the assembled device illustrated in FIGS. 1–3, taken through the portion of the shroud containing the connector block, stabilizer bar and associated components.

FIG. 8 shows a cross-sectional view through the assembly of FIG. 7. In this view, the interrelation of the various components within the portion of shroud 10 which serves as the connector module can be seen. Connector bore 41 is visible in this view and is configured as a stepped bore, having dimensions as specified according to the IS-1 international standard for implantable pacemaker connector assemblies. The proximal end 48 of connector bore 41 is located adjacent connector block 50, and aligned with bore 51 through the connector block 50. Bore 51 is intended to receive a connector pin mounted to the connector assembly of an implantable pacing lead, which pin may extend through bore 51 into recess 46. Set screw 56 is visible in cross-section, located beneath recess 11, which is aligned with an internal recess 17. The portion of the shroud 10 between recesses 11 and 17 defines an access path to set screw 56, which is breached by a set screw wrench, when rotation of set screw 56 is desired to engage or disengage the connector pin of a pacing lead from connector block 50.

Grommet shim 15 serves to assist in maintaining a fluid tight high impedance seal of the connector block assembly in the following manner. After assembly of the connector block 50, stabilizer pin 54 and set screw 56 into shroud 10, shim 15 is inserted into slot 13a in depression 13 (FIG. 4). Shim 15 may be fabricated of any appropriate biocompatible plastic or metal. Shim 15 compresses the material of shroud 10 in the area adjacent thereto to provide uniform compression along the defined access path. Thus, when the set screw wrench is removed after tightening or loosening of set screw 56, shim 15 assists in urging the material of shroud 10 against itself along the defined access path to form a tight seal, preventing fluid leakage from the exterior of the device inward to connector block 50. The point of insertion of shim 15 is sealed with medical adhesive 19.

As illustrated, stabilizer bar 54 is located in a dead-ended recess 53 formed in connector block 50. Because connector block 50 is essentially free-floating within a resilient structure (shroud 10) excessive torque applied to the connector block assembly, when the connector pin of a pacing lead is not inserted into connector block 50, would tend to rotate connector block 50 within shroud 10. Rotation of the connector block within the shroud 10 could prevent insertion of a connector pin, and would likely fracture connector block wire 52. Therefore, stabilizer rod 54 is provided, in order to prevent rotation of connector block 50, relative to shroud 10, even in the absence of an inserted pacing lead connector pin. In order to further enhance the durability of the connector module, connector block wire 52 and corresponding curved slot 73 both follow a generally S-shaped curve, to provide strain relief for connector wire 52.

Figure 9:
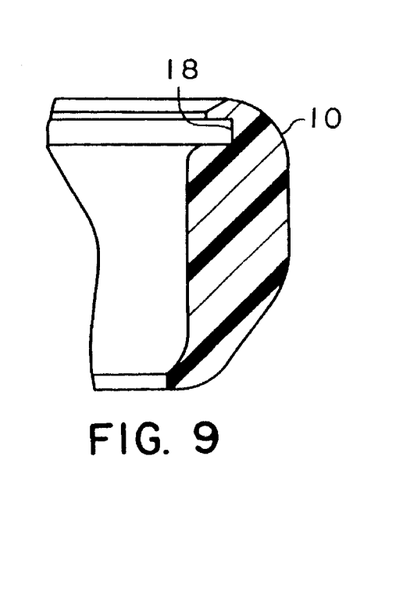
FIG. 9 is a sectional view through a portion of the shroud illustrated in FIGS. 5 and 6.

FIG. 9 shows a sectional view through the shroud 10, as illustrated in FIG. 6. In this view, slot 18, which engages flange 36 of shield 30 and the outer edge of lid 20 is clearly visible.

Figure 10:
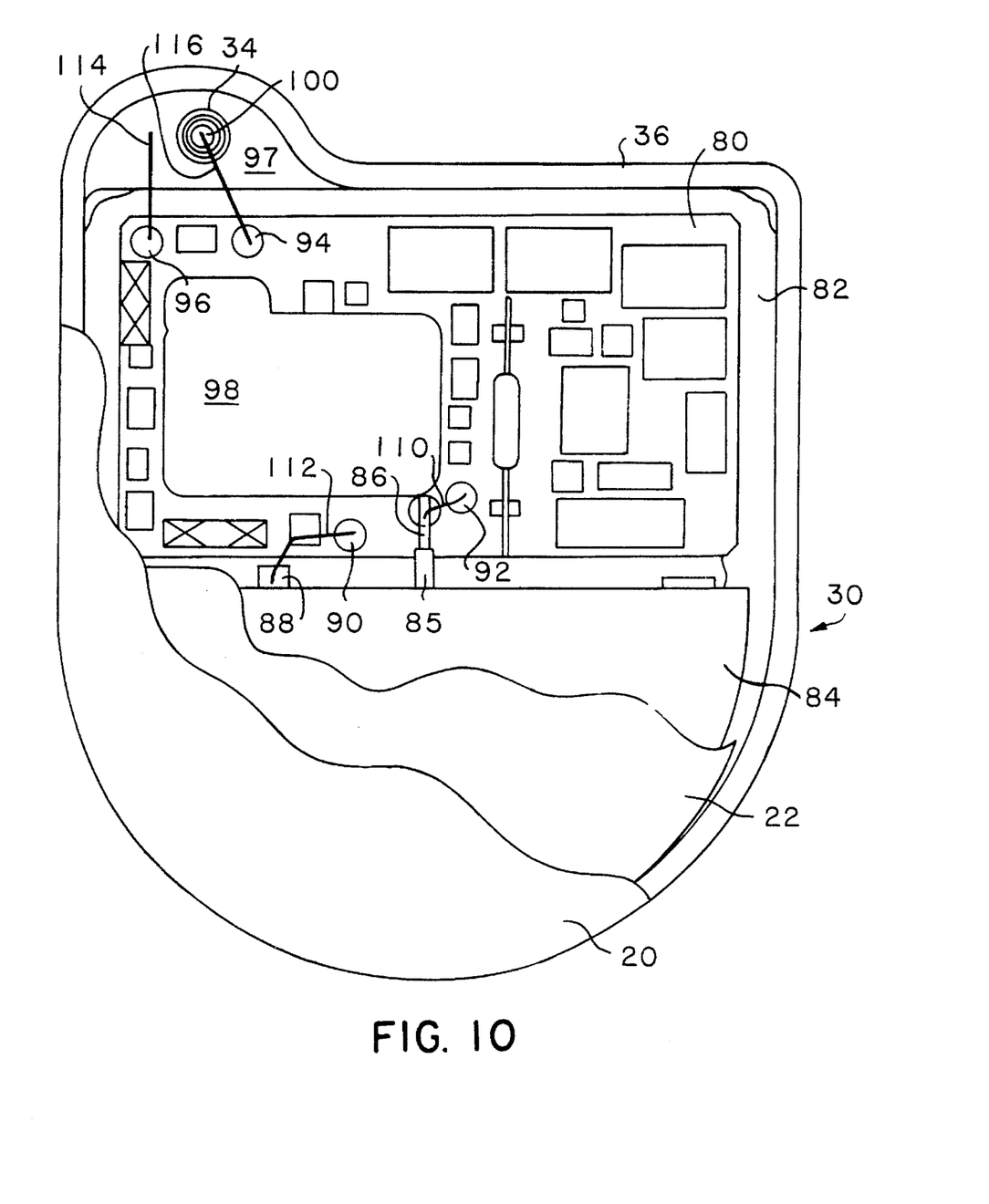
FIG. 10 is a cutaway view of the device housing illustrated in FIG. 4, looking at the housing from the upper surface.

FIG. 10 is a cutaway view through the device housing, illustrating the inter-relation of the components of the housing and the battery, hybrid circuit and feedthrough. In this view, the relative location of the battery 84 and the hybrid 80 can be seen. Hybrid circuit 80 comprises a single large scale integrated circuit located underneath an adhesive die coat covering 98, and discrete, surface mounted components such as large capacitors, a reed switch, a telemetry antenna, and so forth, typically found in pacemaker hybrids, located on a generally planar ceramic substrate. The circuitry may correspond to any known pacemaker circuit. In particular, the hybrid may provide the functions of a multi-programmable WI pacemaker, corresponding generally to those disclosed in U.S. Pat. No. 4,401,120 issued to Hartlaub et al, U.S. Pat. No. 4,958,632, issued to Duggan, U.S. Pat. No. 5,052,388, issued to Sivula et al, U.S. Pat. No. 5,080,096, issued to Hooper et al, U.S. Pat. No. 5,088,488, issued to Markowitz et al, U.S. Pat. No. 5,127,404, issued to Wyborny et al or U.S. Pat. No. 5,154,170, issued to Bennett et al, all of which are incorporated herein in thier entireties.

Typically, in embodiments taking the form of a cardiac pacemaker, a sense amplifier or amplifiers within the pacing circuitry and a pulse generator or generators within the pacing circuitry will be connected to the feedthrough or feedthroughs in the device housing and/or to the housing itself. In the disclosed present embodiment, the device takes the form of a unipolar VVI pulse generator, so both the sense amplifier and the pulse generator within the circuitry 80 are coupled to the feedthrough 34 and to the shield 30 of the device housing. The specific circuitry and the specific functions performed by the circuitry are not claimed as part of the invention, as the invention is believed to be workable in conjunction with circuitry corresponding to any known pacemaker modality, as well as with circuitry associated with other types of implantable devices, such as implantable defibrillators, nerve stimulators, monitors or drug pumps.

Hybrid circuit 80 and battery 84 are mounted to shield 30 by means of adhesive of 82, which replaces the molded plastic cups or clips typically employed in implantable devices for location of battery and hybrid components. The adhesive 82 serves to firmly attach the hybrid and battery to the shield and in some embodiments may also serve to insulate the hybrid and battery from the shield 30.

In evaluating candidate adhesives for use in conjunction with the present invention, a large number of adhesives were tested, with the result that a two-part epoxy, manufactured by Emerson and Cummings, Woburn, Mass., combining epoxy 45SC with catalyst 15SC (Eccobond epoxy) provided an adhesive which met the basic process requirements. Specified process requirements included the ability to cure at or below 60° C., a temperature known to be safe for processing of lithium iodine batteries, a volume resistivity of greater then $10^{10}$ ohm-centimeters, low extractable chloride, fluoride, sodium and potassium, a pot life of at least 30 minutes at 25° C., compatibility with automated dispensing machinery, a viscosity of greater than 60,000 cps a gap filling capacity of greater than 0.040" and the ability to provide a reliable mechanical bond to titanium (shield 30), nickel (stud 88), alumina (hybrid 80) and stainless steel (battery 84).

To fabricate the device housing, an insulative sheet of PET plastic having an outline corresponding to but smaller than the lower surface of the shield is placed into the shield. In some embodiments, this insulator sheet may be omitted, relying only on the adhesive for insulation. The Eccobond adhesive 82 is then dispensed into the shield, following a path along the periphery of the lower surface of the shield 30 and the PET insulator, corresponding to the intended locations of the outer edges of the battery 84 and hybrid 80, and adhesive is also placed at the intended location of the feedthrough wire from the battery. The adhesive is dispensed using a meter mix system manufactured by Liquid Control Corporation, North Canton, Ohio, integrated with an Asymtek A-600C adhesive dispenser, manufactured by Asymtek, Carlsbad, Calif. The hybrid 80 and battery 84 are placed in their desired locations within the shield 30, as illustrated, and cured at 60° C. for 25–30 minutes. The PET insulator prevents the conductive surfaces on the battery 84 and the hybrid 80 from settling through the adhesive to make contact with the shield 30.

Interconnection of the battery 84 with the hybrid 80 and interconnection of the hybrid 80 with the feedthrough 34 and the shield half 38 is accomplished by means of wire bonding, employing heavy aluminum wire bonding processes known for use in the high power electronic device industry, but previously not employed in the context of implantable pacemakers. The fact that the hybrid and battery are firmly adhesively attached to the shield facilitates utilization of wire bonding technology, which would has not been employed to interconnect batteries, hybrids and feedthroughs in pacemakers employing plastic cups or spacers to locate the internal components less rigidly. For purposes of the present invention, five mil annealed bonding wires formed of an alloy of 99.5% aluminum, 0.5% magnesium. Bonding may be performed using a Model 360 ultrasonic wire bonder operating in "Touch Mode-1", manufactured by Orthodyne Electronics, Irvine Calif., allowing ramping up of bond force during the bond process, with bond power settings and force settings determined empirically for the varying materials to be bonded.

In order to permit the use of wire bonding, the battery and feedthrough structures have been particularly optimized. The feedthrough 34 passes through and extends from internal surface 97 (corresponding to outer surface 37, FIG. 4), which is parallel to and located above the generally planar inner surface of the remainder of shield 30. Feedthrough 34 is oriented so that the feedthrough wire 32 (FIG. 4) is perpendicular to the plane of the hybrid 80, and is provided with an enlarged gold wire bonding pad 100, which defines a surface parallel to the plane of the hybrid circuit 80. The pad 100 of the feedthrough 34 is coupled to a wire bonding pad 94 on hybrid 80 by means of aluminum wire 116, which is bonded to pad 94 on hybrid 80 and to pad 100 on feedthrough 34 by means of standard ultrasonic wedge bonding techniques, employing an orthodyne Model 360 wire bonder, as described above. Similarly, aluminum wire 114 is bonded to pad 96 and bonded directly to inner surface 97 of shield 30. Interconnection of the battery 84 with the circuitry on hybrid 80 is accomplished by means of aluminum wires 112 and 110. Wire 112 is bonded to nickel stud 88 which is welded to the stainless steel case of lithium iodide battery 84 and to pad 90. The feedthrough of battery 84 has been modified by flattening the feedthrough wire 86 to form a strap, which has its end located adjacent the upper surface of the hybrid 80, facilitating wire bonding of wire 110 thereto. Plastic sleeve 85 is mounted around the feedthrough wire 86 and serves as insulation. Wire 110 is also bonded to pad 92.

After wire bonding, the lid 20 is tack welded to the shield 30, at spaced locations around flange 36, in order to assure alignment of the lid 20 and the shield 30 during subsequent laser welding. Insulator 22, which insulates the lid 20 from the housing of the battery 84, is a PET plastic sheet which has a self adhesive backing and is applied to the lower surface of lid 20 prior to tack welding. The lid 20 is then laser welded to the shield 30, around the entire circumference of flange 36, completing the process of assembling the device housing and the components therein. Laser welding of the lid 20 to shield 30 may be accomplished using conventional laser welding techniques, corresponding to those previously employed to weld housing halves for implantable devices together.

Figure 11:
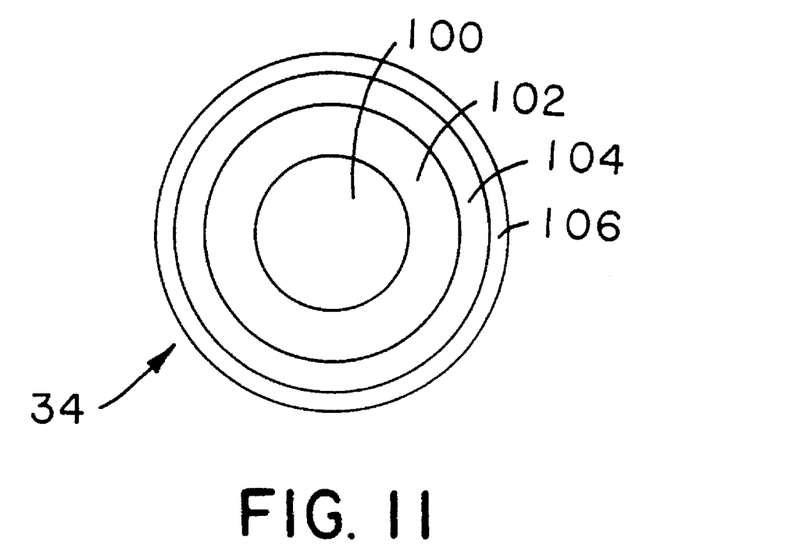
FIG. 11 is a top plan view of the feedthrough mounted to the device housing illustrated in FIG. 10.
Figure 12:
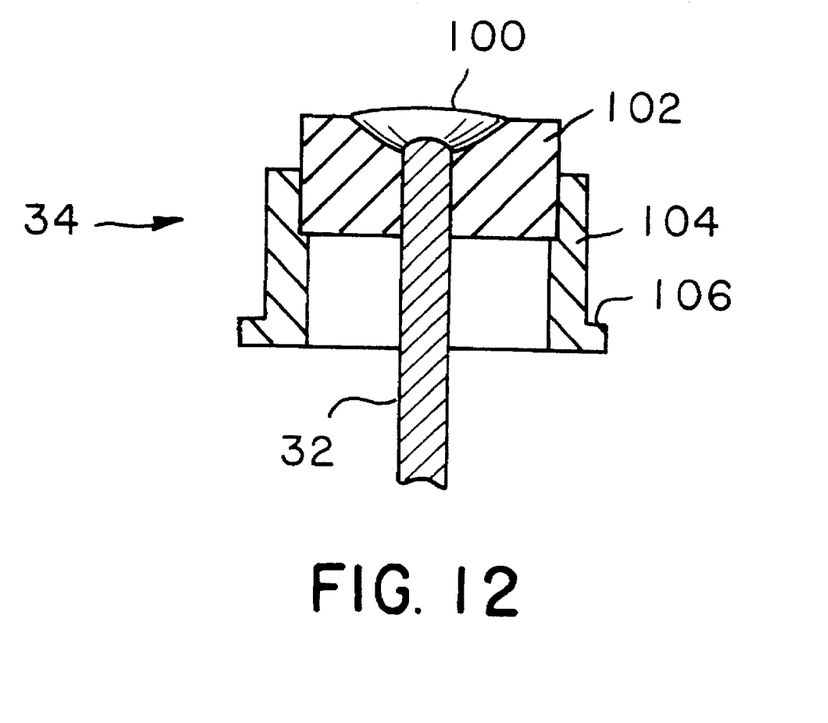
FIG. 12 is a sectional view through the feedthrough illustrated in FIG. 11.

FIGS. 11 and 12 illustrate the feedthrough 34, which is particularly optimized for use in wire bonding operations. Feedthrough 34 corresponds to feedthroughs previously employed in implantable pressure sensors in conjunction with implantable cardiac pacemakers manufactured by Medtronic, Inc. Feedthrough 34 is provided with a ferrule 104, manufactured of titanium and provided with a circumferential flange 106. The insulator 102 is formed of aluminum oxide, sputter coated with niobium in brazing areas, and is brazed to the ferrule 104 using gold as a brazing compound. The terminal pin 132 is fabricated of niobium, and is brazed to the aluminum oxide insulator with a gold brazing compound. During brazing a flat gold bonding pad 100 is formed. Feedthrough 34 is inserted through a circular hole in surface 37 (FIG. 4) of shield 30, with flange 106 contacting the lower surface of shield 30, and is circumferentially laser welded to shield 30. The area of the feedthrough between the ferrule 104 and the feedthrough pin 32 is preferably backfilled with epoxy.

The embodiment specifically disclosed above takes the form of a multi-programmable single chamber (VVI or AAI) pacemaker which employs only a single feedthrough, providing for unipolar pacing and sensing. However, it should be understood that the present invention is equally applicable to pacemaker designs requiring more than one feedthrough, as well as to other implantable device types as discussed above. The basic mechanism of mounting and interconnecting the battery and hybrid circuit disclosed above would be directly applicable in a wide variety of such devices. Similarly, while a specific device housing configuration is illustrated, the present invention provides for the ability to produce device housings and implantable devices in essentially arbitrary configurations. As such, the above disclosure should be taken as exemplary, rather than limiting, with regard to the claims which follow.

What is claimed is:

1. An access grommet assembly for allowing access by a member to a desired location, comprising:

a grommet body means for receiving said member, fabricated of a pliant material and defining an access path for said member to said desired location; and     a shim, embedded in said pliant material adjacent said access path and compressing said pliant material along said access path and sealing said access path when said member is not present in said access path.

2. An access grommet assembly for allowing access to an electrical connector by a tool, comprising:

a grommet body means for receiving said tool, fabricated of a pliant material and defining an access path for said tool to said setscrew; and a shim, embedded in said pliant material adjacent said access path and compressing said pliant material along said access path and sealing said access path when said tool is not present in said access path.

3. An electronic device, comprising:

an electronic circuit;

means for preventing fluid ingress into said circuit;

a connector assembly comprising a connector block coupled to said electronic circuit and an access grommet means for receiving a tool, said access grommet in turn comprising:

a grommet body of a pliant material, mounted external to said connector block and defining a path of access for said tool to said connector block; and a shim, embedded in said pliant material adjacent said access path and compressing said pliant material along said access path and sealing said access path when said tool is not present in said access path.

4. A medical device having an access grommet assembly, comprising:

a hermetic device enclosure;

means within said deice housing for providing a therapeutic treatment;

a grommet body means of a pliant material for receiving a tool, mounted to said device housing and defining an access path for said tool to said means for providing a therapeutic treatment;

a shim, embedded in said pliant material adjacent said access path and compressing said pliant material along said access path and sealing said access path when said tool is not present in said access path.

5. A device as in claim 4, wherein said means within said device housing for providing a therapeutic treatment comprises cardiac pacemaking circuitry.

6. A medical device having an access grommet assembly, comprising:

a hermetic device enclosure;

means within said device housing responsive to physiologic signals;

a grommet body means of a pliant material for receiving a tool, mounted to said device housing and defining an access path for said tool to said responsive means;

a shim, embedded in said pliant material adjacent said access path, compressing said pliant material along said access path and sealing said access path when said tool is not present in said access path.

7. A device as in claim 6, wherein said responsive means comprises cardiac sense amplifier circuitry.

* * * * *